(12) United States Patent
Demanget (10) Patent No.: US 12,399,550 B2
(45) Date of Patent: Aug. 26, 2025

(54) TRIGGERING AN ACQUISITION DURING MIXED-REALITY HEADSET-BASED NAVIGATION

(71) Applicant: DEPUY IRELAND UNLIMITED COMPANY, Ringaskiddy (IE)

(72) Inventor: Nicolas Demanget, Warsaw, IN (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 0 days.

(21) Appl. No.: 18/422,762

(22) Filed: Jan. 25, 2024

(65) Prior Publication Data

US 2025/0244820 A1    Jul. 31, 2025

(51) Int. Cl.
| | |
|---|---|
| G06F 3/04817 | (2022.01) |
| A61B 34/00 | (2016.01) |
| A61B 34/20 | (2016.01) |
| G06F 3/01 | (2006.01) |
| G06T 7/73 | (2017.01) |
| A61B 90/00 | (2016.01) |
| A61B 90/50 | (2016.01) |
| A61B 90/53 | (2016.01) |

(52) U.S. Cl.
CPC ............. *G06F 3/011* (2013.01); *A61B 34/25* (2016.02); *G06F 3/012* (2013.01); *G06F 3/013* (2013.01); *A61B 2034/2068* (2016.02); *A61B 2090/363* (2016.02); *A61B 2090/364* (2016.02); *A61B 2090/365* (2016.02); *A61B 2090/502* (2016.02); *G06T 7/73* (2017.01); *G06T 2200/24* (2013.01); *G06T 2207/30008* (2013.01)

(58) Field of Classification Search
CPC ............ A61B 34/25; A61B 2034/2068; A61B 2090/363; A61B 2090/502; A61B 2090/364; A61B 2090/365; G06F 3/012; G06F 3/013; G06F 3/04815; G06F 3/0487; G06F 3/011; G06T 7/73; G06T 2200/24; G06T 2207/30008; G06T 2210/41
See application file for complete search history.

(56) References Cited

U.S. PATENT DOCUMENTS

| | | | |
|---|---|---|---|
| 8,165,659 B2 * | 4/2012 | Sheffer | A61B 34/20 |
| | | | 600/407 |
| 10,398,514 B2 * | 9/2019 | Ryan | A61B 90/37 |
| 2020/0004328 A1 | 1/2020 | Blume et al. | |
| 2021/0378757 A1 | 12/2021 | Bay et al. | |
| 2022/0151704 A1 * | 5/2022 | Nikou | G16H 40/20 |
| 2023/0233259 A1 * | 7/2023 | Young | A61B 34/25 |
| | | | 606/88 |

\* cited by examiner

*Primary Examiner* — Julie Anne Watko (74) *Attorney, Agent, or Firm* — Flaster Greenberg P.C.

(57) ABSTRACT

Method(s) and device(s) are described herein for mixed-reality (MR) headset-based navigation during a surgical procedure. For example, a surgeon or other medical professional may use a pointer during a surgical procedure to acquire a location of a patient's anatomical landmark. A virtual button may be overlaid on an array of the pointer, and may follow the motion of the pointer if the pointer is moved. An eye gaze and/or a head gaze may be used to launch acquisition of the location of the anatomical landmark. The location of the anatomical landmark may be confirmed by the surgeon.

20 Claims, 6 Drawing Sheets

TRIGGERING AN ACQUISITION DURING MIXED-REALITY HEADSET-BASED NAVIGATION

TECHNICAL FIELD

Various exemplary embodiments disclosed herein relate generally to mixed-reality headset-based navigation.

BACKGROUND

Navigated and robotic surgery may require a patient reference frame to locate a patient in space. Some embodiments may use mixed reality (MR)-based systems. Some MR-based systems may require a surgeon or other medical professional to provide inputs in order to go to a previous/next step, launch/stop an acquisition, and/or accept or reject a pop-up.

SUMMARY

A summary of various exemplary embodiments is presented below. Some simplifications and omissions may be made in the following summary, which is intended to highlight and introduce some aspects of the various exemplary embodiments, but not to limit the scope of the disclosure. Detailed descriptions of an exemplary embodiment adequate to allow those of ordinary skill in the art to make and use the inventive concepts will follow in later sections.

Systems, methods, and apparatus are described herein for mixed-reality (MR) headset-based navigation during a surgical procedure. For example, a surgeon or other medical professional may use a pointer during a surgical procedure to acquire a location, which may be a location of an anatomical landmark on the patient that may be relevant to the surgical procedure. A virtual button may be overlaid on an array of the pointer, and may follow the motion of the pointer if the pointer is moved. An eye gaze and/or a head gaze may be used to launch acquisition of the location of the bone.

For example, various embodiments may include a system (e.g., an MR-based system, which may be part of a computer-aided surgery (CAS) system) that comprises an MR headset, which may itself comprise one or more cameras, a display configured to display a graphical user interface (GUI), one or more inertial measurement unit (IMU) sensors, and/or a processor configured to perform certain steps. The processor may determine a location of a pointer in a field of view of the MR headset camera(s). The pointer may be touched to a patient's anatomy by a user of the MR headset. For example, the pointer may be touched to a most superior point of a glenoid, a most posterior point of a femur, or another part of the patient's anatomy. The processor may cause the display to overlay a virtual button in the field of view and proximate a center of the pointer based on the determined location of the pointer. The processor may cause the display to overlay the virtual button when the pointer is still (e.g., the location of the pointer has not changed within a first threshold amount of time).

The processor may monitor a user-controllable parameter of the headset, for example using information received from the one or more cameras and/or the one or more IMU sensors. The user-controllable parameter may be an eye gaze of the user, and the processor may track the eye gaze using information from the one or more cameras. Alternatively, the user-controllable parameter may be a position of the user's head, and the processor may track the position of the user's head using information from the one or more IMU sensors. The processor may cause the display to overlay a cursor in the field of view, for example if the user-controllable parameter is the position of the user's head. In certain cases, the display may only overlay the cursor in the field of view when the user-controllable parameter is directed to a location that is within a threshold radius of one or more specific points in the field of view (e.g., the virtual button), and may fail to display the cursor if the user-controllable parameter is directed to a location that is not within the threshold radius (es). The processor may cause the display to overlay a first icon within the field of view that, when activated by the user for a second threshold amount of time, allows the user to begin an acquisition procedure, cancel the acquisition procedure, return to a previous step of the acquisition procedure, cancel or delete an acquired anatomical landmark (e.g., the location of the acquired anatomical landmark), and/or restart the acquisition procedure.

The processor may determine that the user-controllable parameter is directed to the virtual button (e.g., the virtual button is being activated by the user). The processor may cause the display to overlay a progress indicator that indicates an amount of time during which the virtual button has been activated. The processor may determine that the user-controllable parameter is directed to the virtual button for at least a third threshold amount of time, and may acquire a location of an anatomical landmark (e.g., one or more points on a bone) based on the user-controllable parameter being directed to the virtual button for at least a second threshold amount of time. The third threshold amount of time may be approximately within the range of one half-second to two seconds. The processor may prompt the user to confirm the acquired location. For example, the processor may cause the display to overlay a popup window in the field of view that displays the acquired location of the anatomical landmark and a second icon that, when activated by the user for a fourth threshold amount of time, cancels the acquired location of the anatomical landmark and restarts the acquisition procedure. If the acquired location is confirmed (e.g., not canceled), the location may be stored in memory for use during a surgical procedure.

BRIEF DESCRIPTION OF THE DRAWINGS

In order to better understand various exemplary embodiments, reference is made to the accompanying drawings.

To facilitate understanding, identical reference numerals have been used to designate elements having substantially the same or similar structure and/or substantially the same or similar function.

DETAILED DESCRIPTION

The description and drawings illustrate the principles of the disclosure. It will thus be appreciated that those skilled in the art will be able to devise various arrangements that, although not explicitly described or shown herein, embody the principles of the disclosure and are included within its scope. Furthermore, all examples recited herein are principally intended expressly to be for pedagogical purposes to aid the reader in understanding the principles of the disclosure and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

One or more of the embodiments disclosed herein may be used with computer-aided surgery (CAS). Before computer-aided surgery takes place, the CAS system learns the locations and relationships of various elements like the patient (e.g., based on images of the patient which might be obtained by a fluoroscopy, x-ray, CT, MRI, etc.) and medical instruments (e.g., scalpel, saw, drill, bone screw, implant, robot, etc.).

The CAS system may include a mixed reality (MR) headset used as part of MR headset-based navigation. The MR headset may be worn by a surgeon (e.g., or other medical professional) during a surgical procedure.

MR headset-based navigation may be used in orthopedics to track instruments in real time, and may provide guidance to surgeons to navigate these instruments accurately relative to the patient's anatomy. The MR headset may include one or more cameras, one or more inertial measurement unit (IMU) sensors, a graphical user interface (GUI) capable of displaying one or more images, and/or a processor.

For example, the MR headset may include one or more cameras that are configured to be pointed outward (e.g., pointing towards a patient during a surgical procedure), and one or more cameras that are configured to be pointed inward (e.g., pointing towards the surgeon's eyes during the surgical procedure).

The MR headset may be used to overlay virtual content on the real world, for example within the surgeon's direct field of view (e.g., just above the patient). The CAS system may require inputs from the surgeon, for example in order to go to a previous/next step, launch/stop an acquisition, and/or accept/reject a pop-up. The CAS system may be used to easily launch an acquisition during an anatomical landmark acquisition process.

Figure 1:
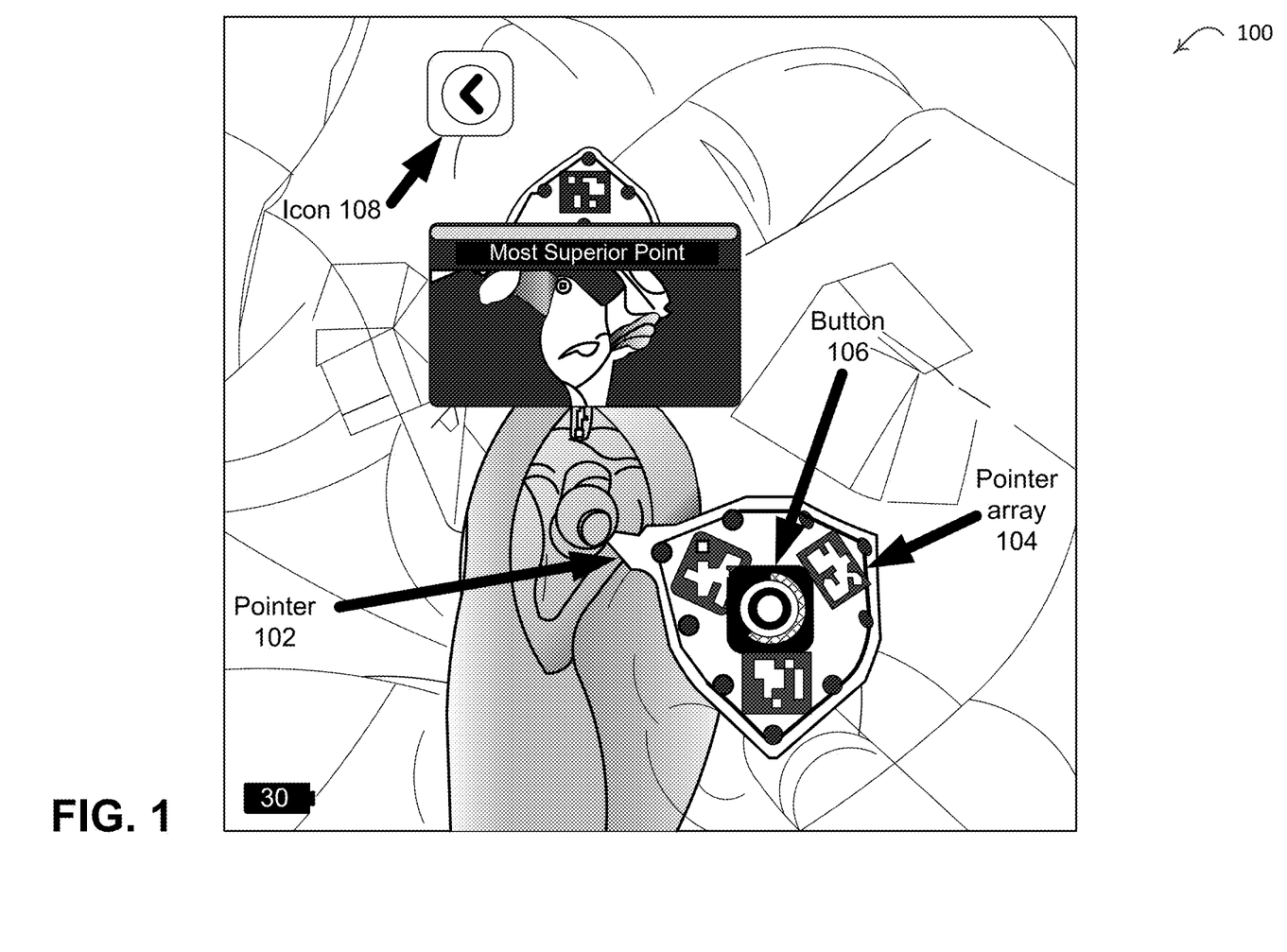
FIGS. 1-3 illustrate examples of images that may be displayed on a graphical user interface (GUI) as part of a surgical procedure.
Figure 2:
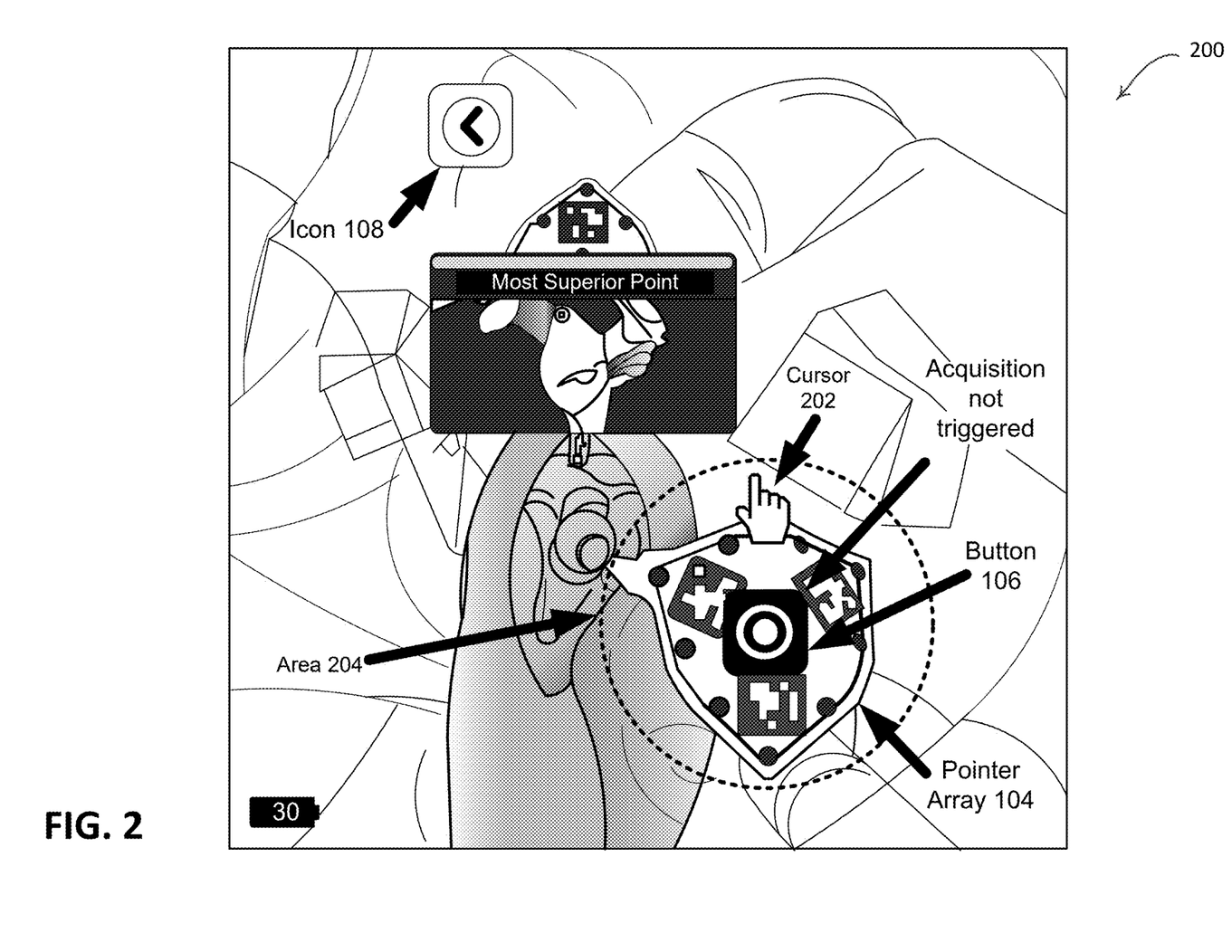
Figure 3:
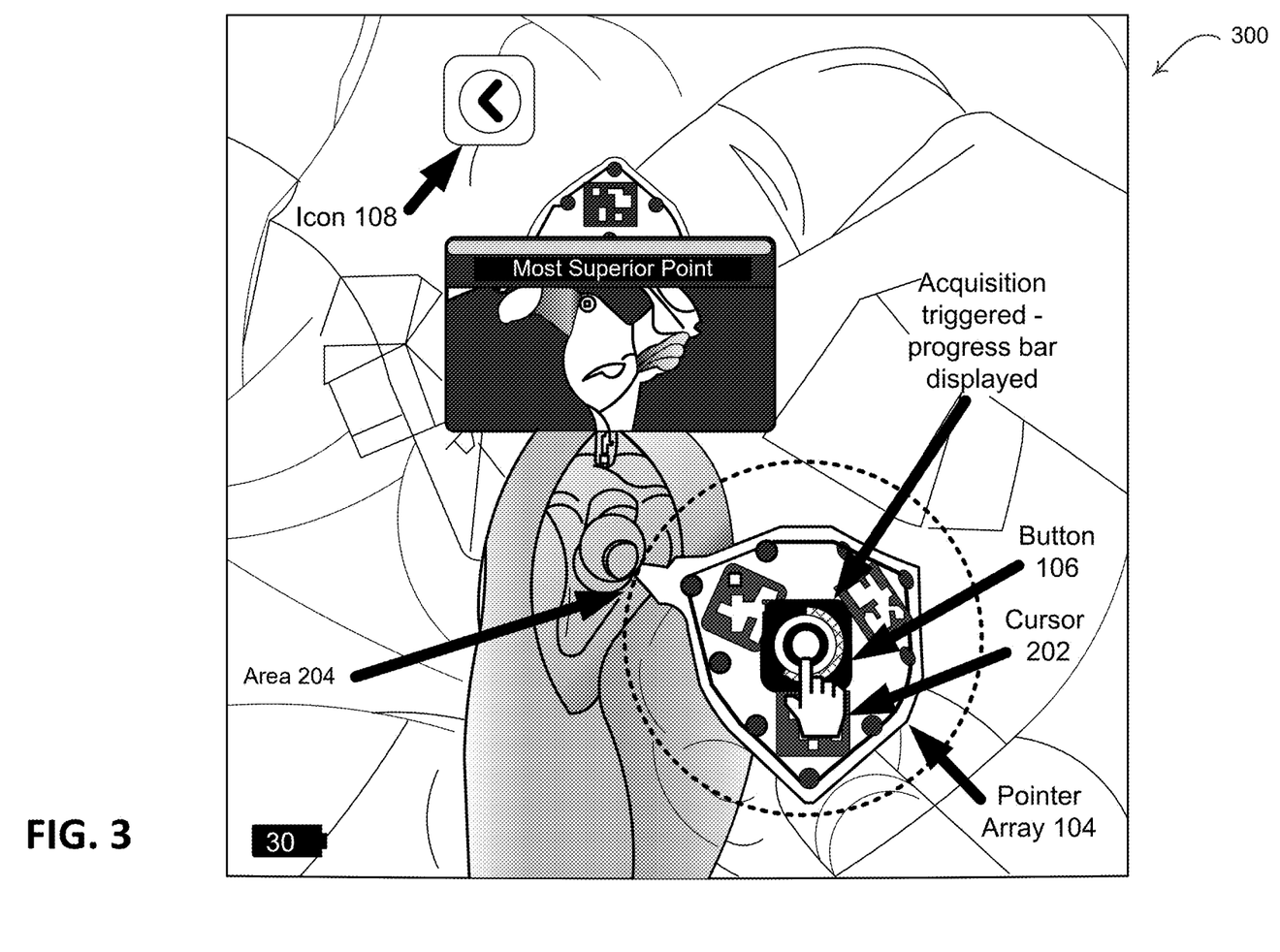

FIGS. 1-3 illustrate examples of images 100, 200, and 300, each of which may be displayed on a graphical user interface (GUI) as part of a surgical procedure. For example, the images 100, 200, and 300 may be displayed on a display of an MR headset that is used by a user (e.g., a surgeon or other medical professional). The images 100, 200, and 300 may include virtual content that is overlaid onto a field of view (e.g., of a patient). For example, as shown in FIGS. 1-3, the images 100, 200, and 300 may overlay virtual content onto a patient's anatomy (e.g., a glenoid or a tibia). The images 100, 200, and 300 may be generated using input from one or more cameras of the MR headset, one or more IMU sensors of the headset, and/or a processor of the headset. The image 100 shown in FIG. 1 may be used as part of a procedure whereby the user's eye gaze is tracked (e.g., using the one or more cameras of the MR headset), and the images 200 and 300 may be used as part of a procedure whereby the user's head gaze (e.g., head position) is tracked (e.g., using the one or more EIUs of the MR headset).

As shown in FIG. 1, the image 100 may include a pointer 102, a pointer array 104, a virtual button 106, and/or an icon 108. The pointer 102 may be a real pointer used by the user, which may have the pointer array 104 printed thereon. The virtual button 106 may be virtual content that is generated by the GUI and overlaid onto the pointer array 104. The virtual button 106 may be moved within the image 100 as the user moves the pointer 102.

The user may use the pointer 102 as part of a procedure to acquire the location of an anatomical landmark (e.g., a point on a patient's bone, which may be a glenoid or a tibia). For example, the location of the anatomical landmark may be acquired in order to perform a registration between a preoperative segmented bone model (e.g., which may be generated using a CT scan or MRI) and the patient's bone intraoperatively. For example, as shown in FIG. 1, the user may touch the pointer 102 to the anatomical landmark (e.g., the most superior point of the bone or the most posterior point of the bone). The MR headset may detect the pointer array 104 (e.g., using information received from the one or more cameras) and may overlay the virtual button 106 onto the pointer array 104 in the image 100. The MR headset may monitor a parameter (e.g., a user-controllable parameter) of the headset (e.g., an eye gaze and/or head position of the user) and may determine that the virtual button 106 is being activated based on the user-controllable parameter and the location of the virtual button 106. In the example shown in FIG. 1, the user-controllable parameter may be an eye gaze of the user, and the MR headset may determine that the virtual button 106 is being activated if the eye gaze of the user is directed to the virtual button 106. The MR headset may wait for a period of time once the eye gaze of the user is directed to the virtual button 106 to determine that the virtual button 106 is being activated in order to ensure that transitory gazes at the virtual button do not erroneously cause the MR headset to determine that the virtual button 106 is being activated.

Once the MR headset determines that the virtual button 106 is being activated, the MR headset (e.g., a processor thereof) may start a timer. The timer may measure an amount of time during which the virtual button 106 is being activated. As shown in FIG. 1, the GUI may display a progress indicator near (e.g., around) the virtual button 106 that indicates an amount of time during which the virtual button 106 has been activated. For example, the progress indicator may be used to instruct the user to continue activating the virtual button 106 until the activation is complete, such that the expected action is triggered.

If the MR headset determines that the virtual button 106 is no longer being activated (e.g., the user's eye gaze is no longer directed to the virtual button 106), the MR headset may stop and/or reset the timer. If the MR headset determines that the virtual button 106 is no longer being activated, the MR headset may stop the timer and wait for an amount of time. If activation of the virtual button 106 resumes within the amount of time, the MR headset may resume the timer. Alternatively, if activation of the virtual button 106 does not resume within the amount of time, the MR headset may reset the timer.

If the virtual button 106 is continuously activated for a threshold amount of time (e.g., approximately 1 to 2 seconds), the MR headset may acquire the anatomical landmark (e.g., the location of the anatomical landmark) using the location of the pointer. For example, the MR headset may acquire a data point (e.g., the end of the pointer) as a point on the anatomical landmark which can be used for registration. Waiting for the threshold amount of time may allow the CAS system to avoid false positives (e.g., where the acquisition of the anatomical landmark is launched inadvertently).

For example, the MR headset may acquire the location of the anatomical landmark after the user's gaze has remained on the virtual button 106 for the threshold amount of time.

Once the location of the anatomical landmark is acquired, the MR headset may prompt the user to confirm the acquired location. For example, the MR headset may overlay a popup (not shown) onto the image 100 that displays the acquired location, an "accept" icon, and/or a "reject" icon. If the user selects the "accept" icon (e.g., by directing their gaze to the "accept" icon for at least a threshold amount of time), the acquired location of the anatomical landmark may be stored in a memory of the MR headset and/or another device. If the user selects the "reject" icon (e.g., by directing their gaze to the "reject" icon for at least a threshold amount of time), the procedure to acquire the location of the anatomical landmark may be performed again. The MR headset may implicitly determine that the acquired location is accepted if the "reject" icon is not selected for at least the threshold amount of time.

The icon 108 may be virtual content that is generated by the GUI and overlaid onto the image 100. For example, the icon 108 may be used to begin an acquisition procedure, cancel the acquisition procedure, return to a previous step of the acquisition procedure, cancel or delete an acquired anatomical landmark (e.g., the location of the acquired anatomical landmark), and/or restart the acquisition procedure. The user may activate (e.g., select) the icon 108 by directing their gaze to the icon for at least a threshold amount of time.

Although FIG. 1 describes the use of an eye gaze of a user as the user-controllable parameter, other options may be used. For example, the examples described in FIGS. 2 and 3 may use a position of the user's head as the user-controllable parameter. As shown in FIG. 2, the images 200 and 300 may include a cursor 202 in addition to the pointer 102, the pointer array 104, the virtual button 106, and/or the icon 108. The pointer 102, pointer array 104, virtual button 106, and/or icon 108 may be as described with reference to FIG. 1.

Referring again to FIG. 2, the cursor 202 may be virtual content that is generated by the GUI and overlaid onto the image 200. The cursor 202 may indicate a position of the user's head, and may move within the image 200 as the position of the user's head moves. The location of the cursor 202 within the image 200 may be determined by the one or more IMU sensors of the MR headset. For example, the position and/or orientation of the user's head may be represented by the cursor, and if the position and/or orientation of the user's head moves, the cursor may move accordingly.

The user may use the pointer 102 and the virtual button 106 as part of a procedure to acquire the location of a anatomical landmark (e.g., as described with reference to FIG. 1 above). For example, the MR headset may determine that the virtual button 106 is being activated when the position of the user's head (e.g., the cursor 202) is directed to the virtual button 106. The MR headset may acquire the location of the anatomical landmark if the virtual button 106 is activated for at least a threshold amount of time.

Once the location of the anatomical landmark is acquired, the MR headset may prompt the user to confirm the acquired location. For example, the MR headset may overlay a popup (not shown) onto the image 100 that displays the acquired location, an "accept" icon, and/or a "reject" icon. If the user selects the "accept" icon (e.g., by directing the cursor 202 to the "accept" icon for at least a threshold amount of time), the acquired location of the anatomical landmark may be stored in a memory of the MR headset and/or another device. If the user selects the "reject" icon (e.g., by directing the cursor 202 to the "reject" icon for at least a threshold amount of time), the procedure to acquire the location of the anatomical landmark may be performed again. The MR headset may implicitly determine that the acquired location is accepted if the "reject" icon is not selected for at least the threshold amount of time.

Although FIG. 2 shows the cursor 202 being overlaid onto the field of view of the image 200, the MR system may fail to overlay the cursor 202 (e.g., may not display or overlay the cursor 202) in certain situations. For example, the cursor 202 may be displayed when the user's head is pointed at a location that is linked to interactable virtual content (e.g., the virtual button 106). Displaying the cursor only when it is within specific areas may avoid visual distractions for the user.

In order to determine whether to display the cursor 202, the MR headset may determine whether the position of the user's head points to a location that is within a threshold distance from a location that is linked to interactable virtual content. For example, the MR headset may fail to display the cursor 202 (e.g., may not display or overlay the cursor 202) if the position of the user's head points to a location that is not within a threshold distance from a location that is linked to interactable virtual content. The threshold distance may be represented by area 204 and may be, for example, a 10-centimeter (cm) diameter circular area around the pointer array 104 and/or the virtual button 106. The area 204 may be of any shape and/or size, and may be pre-configured and/or set by the user at the start of the surgical procedure. The shape and/or size of the area may differ depending on the specific location that is linked to interactable virtual content. For example, the area 204 around the pointer array 104 may have a first size and shape, and an area (not shown) around the icon 108 may have a second size and shape.

As shown in FIGS. 2 and 3, acquisition of the anatomical landmark may be triggered when the position of the user's head (e.g., the cursor 202) is directed to the virtual button 106. The acquisition may be performed as described with respect to FIG. 1.

Figure 4:
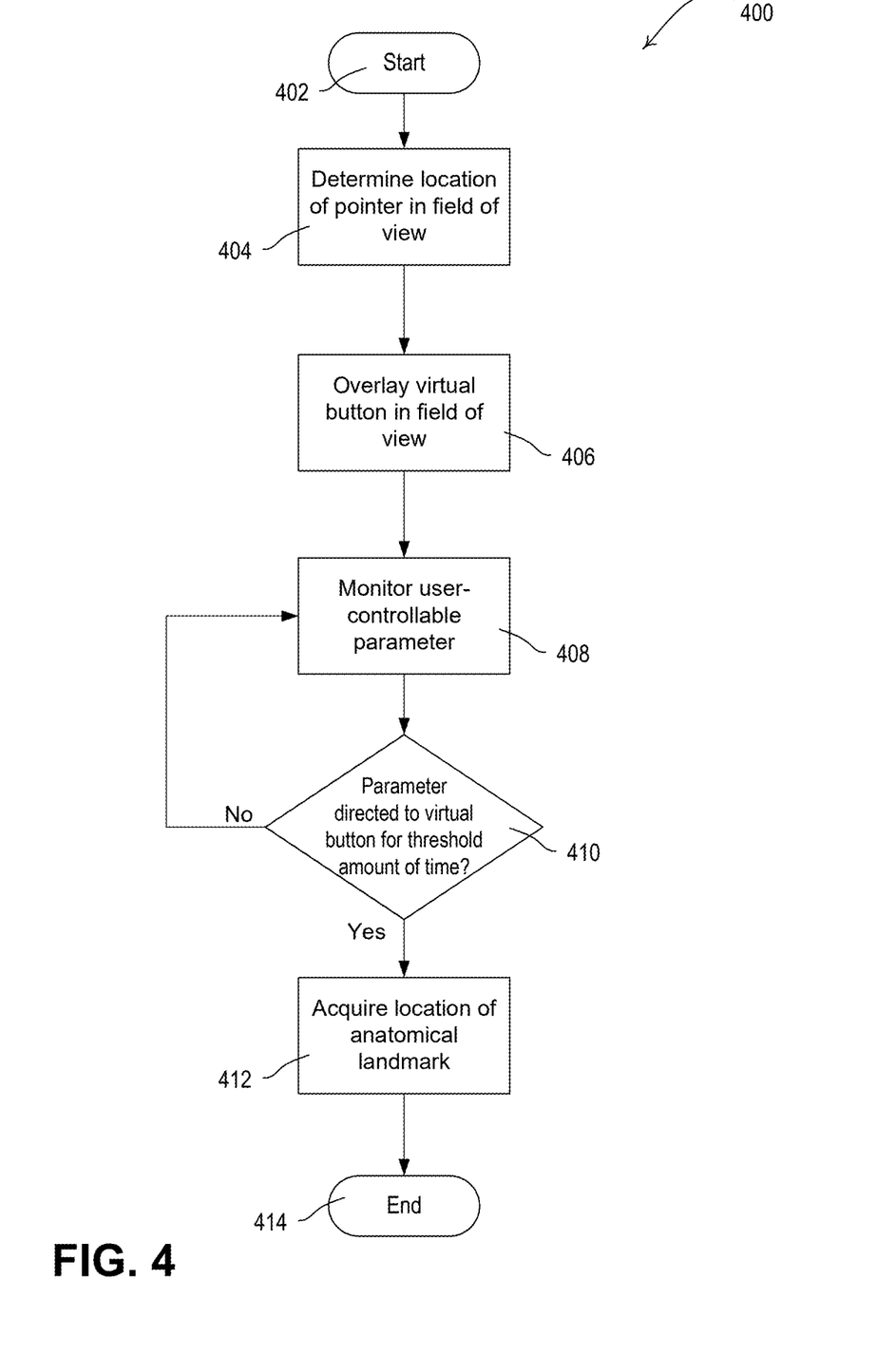
FIG. 4 is a flowchart of an example procedure using a mixed reality (MR)-based system during a surgical procedure.

FIG. 4 is a flowchart of an example procedure 400 using a mixed reality (MR)-based system during a surgical procedure. The procedure 400 may be performed by an MR headset worn by a user (e.g., a surgeon or other medical professional). The MR headset may be a part of a CAS system. The MR headset may include a processor, one or more cameras, one or more IMU sensors, and/or a memory. The procedure 400 may be stored in the memory as computer-readable or machine-readable instructions that may be executed by the processor of one or more devices for executing the procedure 400. The memory may be communicatively coupled to the processor. Though the procedure 400 may be described herein as being performed by a single device, such as a processor, the procedure 400, or portions thereof, may be performed by another device or distributed across multiple devices, such as a wired/wireless processor and/or one or more other devices.

The procedure 400 may begin at 402. At 404, the processor may determine a location of a pointer in a field of view. For example, the field of view may be displayed via a GUI of the MR headset. The pointer may be the pointer 102 described with reference to FIGS. 1-3, and may be printed with a pointer array, which may be the pointer array 104 described with reference to FIGS. 1-3. The pointer may be used as part of the surgical procedure, and may be used to determine the location of one or more anatomical landmarks.

Referring again to FIG. 4, the processor may determine the location of the pointer based on one or more outward-facing cameras of the MR headset. For example, the outward-facing cameras may be pointed away from the user. The processor may determine the location of the pointer by detecting the pointer array in the field of view.

After the processor has determined the location of the pointer in the field of view at 404, the processor may overlay a virtual button in the field of view (e.g., on the GUI of the MR headset) at 406. The processor may overlay the virtual button proximate the pointer using the determined location of the pointer. For example, the virtual button may be overlaid proximate a center of the pointer (e.g., over the pointer array). The processor may wait to overlay the virtual button until the processor determines that the pointer has remained still (e.g., the location of the pointer has not changed) for a threshold amount of time.

At 408, the processor may monitor a user-controllable parameter of the MR headset. For example, the user-controllable parameter may be an eye gaze of the user, and the processor may track the eye gaze using one or more inward-facing cameras. Alternatively, the user-controllable parameter may be a position of the user's head, and the processor may track the position of the user's head using the one or more IMU sensors.

The processor may cause the GUI to display a cursor within the field of view based on the user-controllable parameter. For example, the cursor may be displayed if the user-controllable parameter is the position of the user's head. The location of the cursor within the field of view may be based on the user-controllable parameter. For example, as the position of the user's head moves, the cursor may move within the field of view correspondingly. The cursor may be hidden (e.g., not displayed) if the user-controllable parameter is directed to a location that is not within a threshold radius of a point that is linked to interactable content, and may be displayed when the user-controllable parameter is directed to a location that is within a threshold radius of a point that is linked to interactable content. For example, the cursor may be hidden if the user-controllable parameter is directed to a location outside a threshold radius of the virtual button, and may be displayed if the user-controllable parameter is directed to a location within the threshold radius of the virtual button.

Figure 6A:
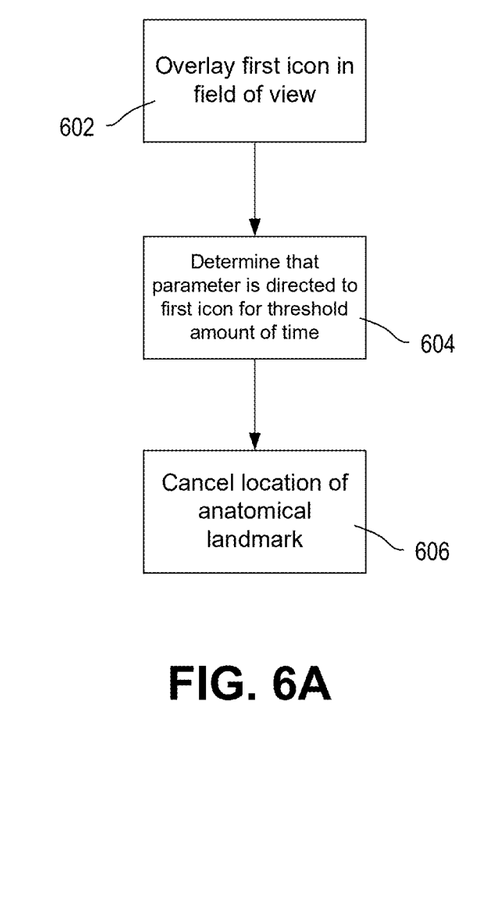
FIGS. 6A and 6B are flowcharts of example procedures using a mixed reality (MR)-based system.
Figure 6B:
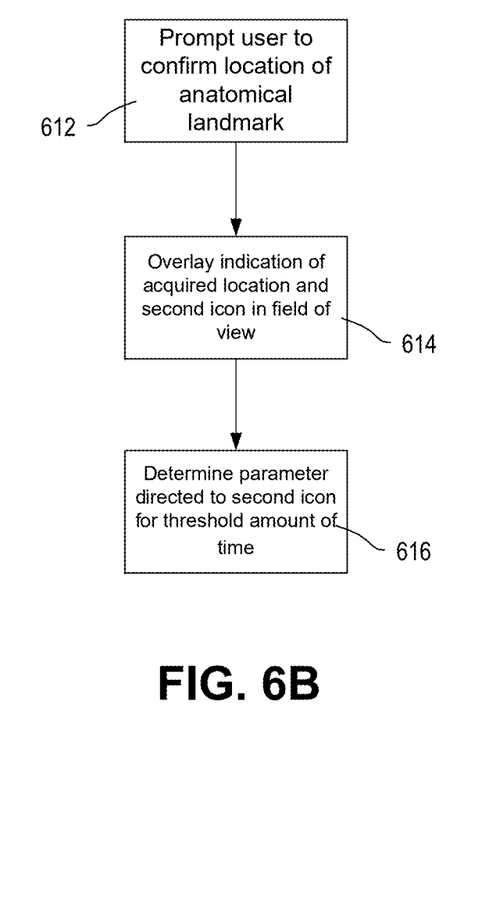

FIGS. 6A and 6B are flowcharts of example procedures using a mixed reality (MR)-based system that may be performed as part of the procedure 400. As part of monitoring the user-controllable parameter, the processor may at 602 overlay an icon in the field of view that, when activated, allows the user to begin an acquisition procedure, cancel the acquisition procedure, return to a previous step of the acquisition procedure, cancel or delete an acquired anatomical landmark (e.g., the location of the acquired anatomical landmark) at 606, and/or restart the acquisition procedure. The icon may be the icon 108 described with respect to FIG. 1. For example, the processor may determine that the icon is activated when the user-controllable parameter is directed to the icon for at least a threshold amount of time at 604.

Referring again to FIG. 4, while monitoring the user-controllable parameter at 408, the processor may detect that the user-controllable parameter is directed to the virtual button (e.g., virtual button is being activated). At 410, the processor may determine whether the user-controllable parameter is directed to the virtual button for at least a threshold amount of time, for example based on information received from the one or more inward-facing cameras and/or the IMU sensor. The processor may determine that the user-controllable parameter is directed to the virtual button if the user's eye gaze and/or the position of the user's head is directed to the virtual button, and may then determine that the virtual button is being activated. The threshold amount of time may be approximately within the range of one half-second to two seconds.

Once the processor determines that the user-controllable parameter is directed to the virtual button, the processor may start a timer. There may be a delay between the processor determining that the user-controllable parameter is directed to the virtual button and the processor starting the timer to ensure that the activation of the button is not a transitory and/or unintended activation. The timer may run until the user-controllable parameter is no longer directed to the virtual button or the threshold amount of time has been reached, whichever comes first. While the user-controllable parameter is directed to the virtual button, the processor may cause the GUI to display a progress indicator within the field of view that indicates the amount of time during which the virtual button has been activated. Although FIGS. 1 and 3 illustrate the progress indicator as being a circular bar around the virtual button, the progress indicator may be in any shape, size, or location. For example, the progress indicator may be used to instruct the user to continue activating the virtual button 106 until the activation is complete, such that the expected action is triggered.

Referring again to FIG. 4, if the processor determines that the user-controllable parameter is no longer directed to the virtual button, and the threshold amount of time has not yet been reached, the processor may pause the timer and may wait for a period of time. If the activation of the virtual button resumes during the period of time, the processor may resume the timer. If the activation of the virtual button does not resume during the period of time, the processor may reset the timer. If the processor resets the timer, or if the processor otherwise determines that the user-controllable parameter is not directed to the virtual button for at least the threshold amount of time, the processor may resume monitoring the user-controllable parameter, and the procedure 400 may return to 408.

If the processor determines at 410 that the user-controllable parameter is directed to the virtual button for at least the threshold amount of time, the processor may acquire a location of an anatomical landmark (e.g., may acquire the anatomical landmark) at 412. The anatomical landmark may be any anatomical landmark on a patient's anatomy. For example, the anatomical landmark may be a point on a bone that is part of a joint (e.g., a glenoid or humerus for the shoulder, a femur or a tibia for the knee, a pelvis or femur for the hip, etc.), a bone itself, and/or the like. The location of the anatomical landmark may be the location of the anatomical landmark relative to the patient's anatomy (e.g., the location of the most superior point of a glenoid or a most posterior point of a tibia). The acquired location of the anatomical landmark may be used to acquire data on a bone for use during a surgical procedure. For example, the acquired location of the anatomical landmark may be used as part of the attachment of a ligament to a bone. The processor may acquire the location of the anatomical landmark based on the location of the pointer and/or the pointer array. For example, the processor acquiring the location of the anatomical landmark may include the processor reading a point in space and using it as a point for registration of the anatomical landmark.

Referring again to FIG. 6B, once the location of the anatomical landmark is acquired, the processor may prompt the user to confirm the location of the anatomical landmark at 612. For example, the processor may cause the GUI to display the prompt within the field of view at 614. The prompt may display the acquired location of the anatomical landmark and/or one or more icons. For example, the one or more icons may include an "accept" icon and/or a "reject" icon, and the user may confirm the location of the anatomical landmark by directing the user-controllable parameter to the "accept" icon for at least a threshold amount of time, and reject the location of the anatomical landmark by directing the user-controllable parameter to the "reject" icon for at least a threshold amount of time at 616. Alternatively, the GUI may display the "reject" icon only, and the processor may determine that the location of the anatomical landmark is confirmed after a given period if the user does not direct the user-controllable parameter to the "reject" icon for the threshold amount of time. Referring again to FIG. 4, if the user rejects the acquired location, the processor may restart the procedure 400 in order to acquire the correct location of the anatomical landmark. Otherwise, the procedure 400 may end at 414.

Figure 5:
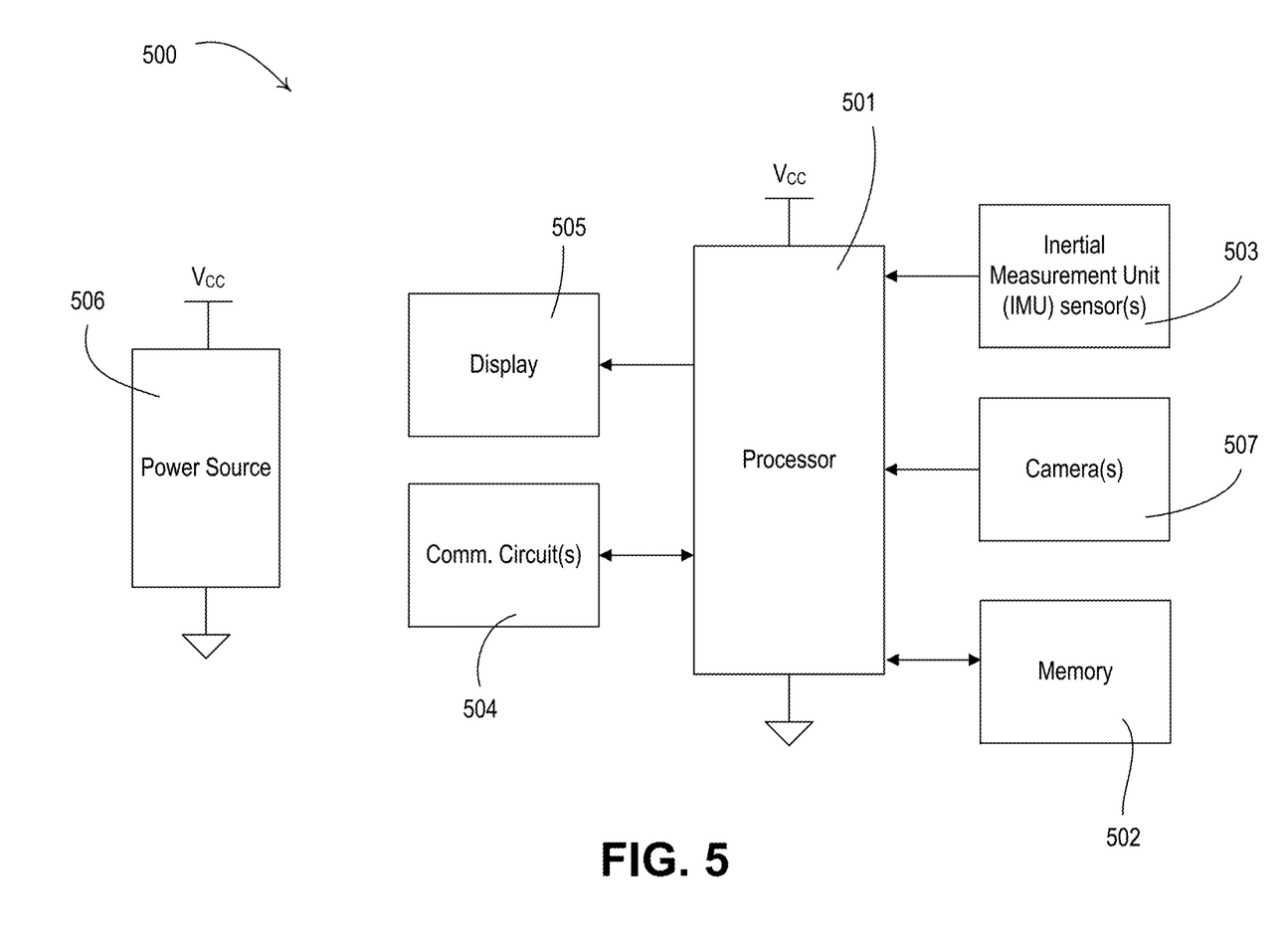
FIG. 5 is a block diagram illustrating an example of a device that may be used in an MR-based system.

FIG. 5 is a block diagram illustrating an example of a device 500 that may be used in an MR-based system. For example, the device 500 may be an MR headset.

The device 500 may include a processor 501 for controlling the functionality of the device 500. The processor 501 may include one or more general purpose processors, special purpose processors, conventional processors, digital signal processors (DSPs), microprocessors, integrated circuits, a programmable logic device (PLD), application specific integrated circuits (ASICs), and/or the like. The processor 501 may perform any functionality that enables the device 500 to perform as described herein. For example, the processor 501 may perform one or more of the steps of the procedure 400.

The processor 501 may be communicatively coupled to a memory 502, and may store information in and/or retrieve information from the memory 502. The memory 502 may comprise computer-readable storage media and/or machine-readable storage media that maintains any values or indicators described herein, and/or computer-executable instructions for performing as described herein. For example, the memory 502 may comprise computer-executable instructions or machine-readable instructions that include one or more portions of the procedures described herein. The processor 501 may access the instructions from memory 502 for being executed to cause the processor 501 to operate as described herein, or to operate one or more other devices as described herein. The memory 502 may comprise computer-executable instructions for executing configuration software and/or control software. The computer-executable instructions may be executed to perform one or more procedures described herein.

The memory 502 may include a non-removable memory and/or a removable memory. The non-removable memory may include random-access memory (RAM), read-only memory (ROM), a hard disk, and/or any other type of non-removable memory storage. The removable memory may include a subscriber identity module (SIM) card, a memory stick, a memory card, and/or any other type of removable memory. The memory 502 may be implemented as an external integrated circuit (IC) or as an internal circuit of the processor 501.

The device 500 may include one or more communication circuits 504 that are in communication with the processor 501 for sending and/or receiving information as described herein. The communication circuit 504 may perform wireless and/or wired communications. The communication circuit 504 may be a wired communication circuit capable of communicating on a wired communication link. The wired communication link may include an Ethernet communication link, an RS-485 serial communication link, a 0-10 volt analog link, a pulse-width modulated (PWM) control link, and/or another wired communication link. The communication circuit 504 may be configured to communicate via power lines (e.g., the power lines from which the device 500 receives power) using a power line carrier (PLC) communication technique. The communication circuit 504 may be a wireless communication circuit including one or more RF or infrared (IR) transmitters, receivers, transceivers, and/or other communication circuits capable of performing wireless communications.

Though a single communication circuit 504 is illustrated in FIG. 5, multiple communication circuits may be implemented in the device 500. The device 500 may include a communication circuit configured to communicate via one or more wired and/or wireless communication networks and/or protocols, and at least one other communication circuit configured to communicate via one or more other wired and/or wireless communication networks and/or protocols. For example, a first communication circuit may be configured to communicate via a wired or wireless communication link, while another communication circuit may be capable of communicating on another wired or wireless communication link. The first communication circuit may be configured to communicate via a first wireless communication link (e.g., a wireless network communication link) using a first wireless protocol (e.g., a wireless network communication protocol), and the second communication circuit may be configured to communicate via a second wireless communication link (e.g., a short-range or direct wireless communication link) using a second wireless protocol (e.g., a short-range wireless communication protocol).

The processor 501 may be in communication with one or more inertial measurement unit (IMU) sensor(s) 503, from which inputs may be received. For example, the IMU sensor(s) may be used to tack a position of a head (e.g., a head gaze) of a user of the device 500.

The processor 501 may be in communication with a display 505. The display 505 may be a visible display for providing information (e.g., feedback) to a user. The processor 501 and/or the display may generate a graphical user interface (GUI) generated via software for being displayed on the device 500 (e.g., on the display 505 of the device 500). For example, the display 505 may display a field of view that includes a patient's anatomy. The GUI may be a mixed-reality GUI, whereby virtual content is overlaid (e.g., by the processor 501) onto one or more real-world objects in the field of view.

Each of the hardware circuits within the device 500 may be powered by a power source 506. The power source 506 may include a power supply configured to receive power from an alternating-current (AC) power supply or direct-current (DC) power supply, for example. The power source 506 may produce a supply voltage for powering the hardware within the device 500.

The processor 501 may be in communication with one or more camera(s) 507. For example, the one or more camera(s) 507 may include one or more outward-facing camera(s) and one or more inward-facing camera(s). The outward-facing camera(s) may be used to observe the patient's anatomy and may provide information to the display 505 (e.g., via the processor). The outward-facing camera may be used (e.g., in conjunction with the processor) to determine the location of one or more pointers as described herein. The inward-facing camera(s) may be used to track an eye gaze of the user, and may provide information to the display 505 (e.g., via the processor).

Although the various exemplary embodiments have been described in detail with particular reference to certain exemplary aspects thereof, it should be understood that the disclosure is capable of other embodiments and its details are capable of modifications in various obvious respects. As is readily apparent to those skilled in the art, variations and modifications and combinations of the various embodiments can be affected while remaining within the spirit and scope of the disclosure. Accordingly, the foregoing disclosure, description, and figures are for illustrative purposes only and do not in any way limit the disclosure, which is defined only by the claims.

What is claimed is:

1. A method comprising:
   determining a location of a pointer in a field of view of a mixed reality (MR) headset of a user;
   overlaying a virtual button in the field of view and proximate the pointer based on the location of the pointer;
   monitoring a parameter of the headset, wherein the parameter is controllable by the user;
   determining that the user-controllable parameter is directed to the virtual button for at least a threshold amount of time; and
   acquiring a location of an anatomical landmark on a patient's anatomy based on determining that the user-controllable parameter is directed to the virtual button for at least the threshold amount of time.

2. The method of claim 1, wherein overlaying the virtual button in the field of view and proximate the pointer comprises:
   determining that the location of the pointer has not changed within a second threshold amount of time; and
   overlaying the virtual button in the field of view and proximate the pointer based on determining that the location of the pointer has not changed within the second threshold amount of time.

3. The method of claim 1, wherein monitoring the user-controllable parameter comprises tracking an eye gaze of the user or a position of a head of the user.

4. The method of claim 1, further comprising overlaying a cursor in the field of view based on the user-controllable parameter.

5. The method of claim 4, further comprising:
   determining that the user-controllable parameter is directed to the location that is not within the threshold distance of the virtual button; and
   not overlaying the cursor in the field of view based on determining that the user-controllable parameter is directed to a location that is not within the threshold distance of the virtual button.

6. The method of claim 1, further comprising:
   determining that the virtual button is being activated; and
   overlaying, in the field of view, a progress indicator that indicates an amount of time during which the virtual button has been activated.

7. The method of claim 1, wherein the location of the anatomical landmark comprises a location of one or more points on a bone of the patient.

8. The method of claim 1, wherein the threshold amount of time is approximately within a range of one half-second to two seconds.

9. The method of claim 1, further comprising:
   overlaying a first icon in the field of view;
   determining that the user-controllable parameter is directed to the first icon for at least a third threshold amount of time; and
   canceling the location of the anatomical landmark based on determining that the user-controllable parameter is directed to the first icon for at least the third threshold amount of time.

10. The method of claim 1, further comprising prompting the user to confirm the acquired location of the anatomical landmark, wherein prompting the user to confirm the acquired location of the anatomical landmark comprises:
    overlaying, in the field of view, an indication of the acquired location of the anatomical landmark and a second icon; and
    determining that the user-controllable parameter is directed to the second icon for at least a fourth threshold amount of time.

11. A device comprising:
    a graphical user interface (GUI) configured to display a mixed reality (MR) field of view to a user; and
    a processor configured to:
    determine a location of a pointer in the field of view;
    cause the GUI to overlay a virtual button in the field of view and proximate the pointer based on the location of the pointer;
    monitor a parameter, wherein the parameter is controllable by the user;
    determining that the user-controllable parameter is directed to the virtual button for at least a threshold amount of time; and
    acquiring a location of an anatomical landmark based on determining that the user-controllable parameter is directed to the virtual button for at least the threshold amount of time.

12. The device of claim 11, wherein the processor being configured to cause the GUI to overlay the virtual button in the field of view and proximate the pointer comprises the processor being configured to:
    determine that the location of the pointer has not changed within a second threshold amount of time; and
    cause the GUI to overlay the virtual button in the field of view and proximate the pointer based on the determination that the location of the pointer has not changed within the second threshold amount of time.

13. The device of claim 11, wherein the device further comprises a camera and an initial measurement unit (IMU) sensor, and wherein the processor being configured to monitor the user-controllable parameter comprises the processor being configured to track, using information received from the camera, an eye gaze of the user or the processor being configured to track, using information received from the IMU sensor, a position of a head of the user.

14. The device of claim 11, wherein the processor is further configured to cause the GUI to overlay a cursor in the field of view based on the user-controllable parameter.

15. The device of claim 14, wherein the processor is further configured to:
    determine that the user-controllable parameter is directed to a location that is not within a threshold distance of the virtual button; and
    cause the GUI to not overlay the cursor in the field of view based on the determination that the user-controllable parameter is directed to the location that is not within the threshold distance of the virtual button.

16. The device of claim 11, wherein the processor is further configured to:
    determine that the virtual button is being activated; and cause the GUI to overlay in the field of view a progress indicator that indicates an amount of time during which the virtual button has been activated.

17. The device of claim 11, wherein the location of the anatomical landmark comprises a location of one or more points on a bone of the patient.

18. The device of claim 11, wherein the threshold amount of time is approximately within a range of one to two seconds.

19. The device of claim 11, wherein the processor is further configured to:
cause the GUI to overlay a first icon in the field of view;
determine that the user-controllable parameter is directed to the first icon for at least a third threshold amount of time; and
cancel the location of the anatomical landmark based on the determination that the user-controllable parameter is directed to the first icon for at least the third threshold amount of time.

20. The device of claim 11, wherein the processor is further configured to prompt the user to confirm the acquired location of the anatomical landmark, wherein the processor being configured to prompt the user to confirm the acquired location of the anatomical landmark comprises the processor being configured to:
cause the GUI to overlay, in the field of view, an indication of the acquired location of the anatomical landmark and a second icon; and
determine that the user-controllable parameter is directed to the second icon for at least a fourth threshold amount of time.

\* \* \* \* \*